United States Patent
Delfino et al.

(10) Patent No.: US 6,626,815 B1
(45) Date of Patent: Sep. 30, 2003

(54) METHOD AND APPARATUS CREATING A RADIOACTIVE LAYER ON A RECEIVING SUBSTRATE FOR IN VIVO IMPLANTATION

(75) Inventors: Michelangelo Delfino, Los Altos, CA (US); Mary E. Day, Los Altos, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

(21) Appl. No.: 09/460,509

(22) Filed: Dec. 9, 1999

Related U.S. Application Data

(62) Division of application No. 08/987,794, filed on Dec. 10, 1997, now Pat. No. 6,129,658.

(51) Int. Cl.$^7$ .............................................. A61N 5/00
(52) U.S. Cl. ........................................................ 600/3
(58) Field of Search ...................... 600/1–8; 424/1.11, 424/1.29

(56) References Cited

U.S. PATENT DOCUMENTS

| | | | |
|---|---|---|---|
| 3,927,325 A | 12/1975 | Hungate et al. ............ 250/435 |
| 5,059,166 A | 10/1991 | Fischell |
| 5,176,617 A | 1/1993 | Fischell |
| 5,213,561 A | 5/1993 | Weinstein et al. ............. 600/7 |
| 5,411,466 A | 5/1995 | Hess ............................. 600/3 |
| 5,484,384 A | 1/1996 | Fearnot ......................... 600/3 |
| 5,503,613 A | 4/1996 | Weinberger ................... 600/3 |
| 5,571,166 A | 11/1996 | Dinh et al. .................... 623/1 |
| 5,624,372 A | 4/1997 | Liprie ............................ 600/3 |
| 5,643,171 A | 7/1997 | Bradshaw et al. ............. 600/1 |
| 5,662,580 A | 9/1997 | Bradshaw et al. |
| 5,871,436 A * | 2/1999 | Eury ............................. 600/3 |

FOREIGN PATENT DOCUMENTS

| | | |
|---|---|---|
| EP | 0 433 011 B1 | 6/1991 |
| EP | 0 593 136 A1 | 4/1994 |
| EP | 0 819 446 A | 1/1998 |
| WO | 92/03179 | 3/1992 |
| WO | WO 97 19706 A | 6/1997 |
| WO | WO 97 38730 A | 10/1997 |
| WO | WO 98 48851 A | 11/1998 |

OTHER PUBLICATIONS

Article by Waksman et al., entitled "Intracoronary Radiation Before Stent Implantation Inhibits Neointima Formation in Stented Procine Coronary Arteries", published in *Circulation*, vol. 92, No. 6 pp. 1383–1386, Sep. 15, 1995.

Alfred Douty and Ellsworth A. Stockbower, entitled "Surface Protection and Finishing Treatments—A. Phosphate Coating Processes", published by Reinhold Publishing Corporation, *Electroplating Engineering Handbook*, pp. 396–401.

Article by Plattner et al., entitled "The Growth of Large, Laser Quality $Nd_xRE_{1-x}P^5O_{14}$ Crystals", published in *Journal of Crystal Growth*, vol. 49, pp. 274–290, 1980.

Article by Prestwich, et al., entitled "The dose distribution produced by a $^{32}$P–coated stent", published in *Med. Phys.*, vol. 22, No. 3, pp. 313–320, Mar. 1995.

Article by Michael A. Streicher, entitled Phosphatization of Metallic Surfaces, published in *Metal Finishing*, pp. 61–69, Aug. 1948.

Article by Hehrlein, et al., entitled "Pure β–Particle–Emitting Stents Inhibit Neiontima Formation in Rabbits", published in *Circulation*, vol. 93, No. 4, pp. 641–645, Feb. 15, 1996.

Article by Carter, et al., entitled "Effects of Endovascular Radiation From a β–Particle–Emitting Stent in a Porcine Coronary Restenosis Model—A Dose Response Study", published in *Circulation*, vol. 94, No. 10, pp. 2364–2368, Nov. 15, 1996.

\* cited by examiner

*Primary Examiner*—Eric F. Winakur

(57) ABSTRACT

An apparatus and method of forming a radioactive stent having a radioactive layer. A solution containing a radioactive isotope depositing substance in solution is provided and placed into contact with the stent or any other substrate material capable of receiving the radioactive isotope. The radioactive isotope is deposited on the stent or substrate material. Preferably a phosphorous isotope is used and the solution is polymerized forming polymer chains containing the radioactive isotope. In this embodiment, the phosphorous is bonded with the substrate material in a phosphorous-oxygen-phosphorous network.

6 Claims, 3 Drawing Sheets

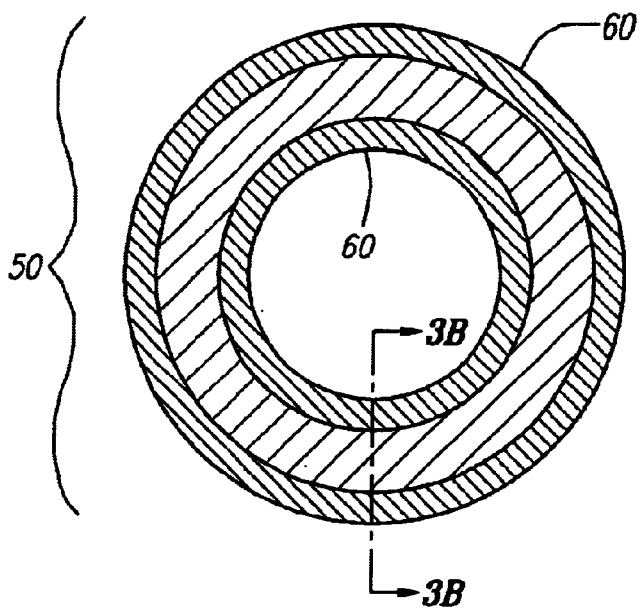
FIG. 3A
FIG. 3B
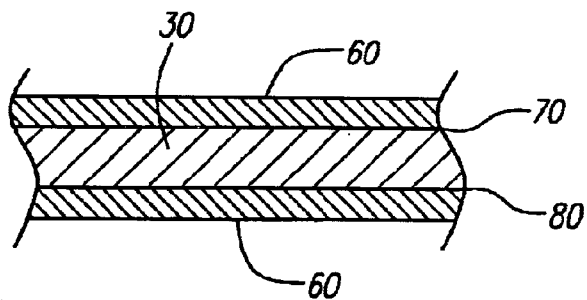
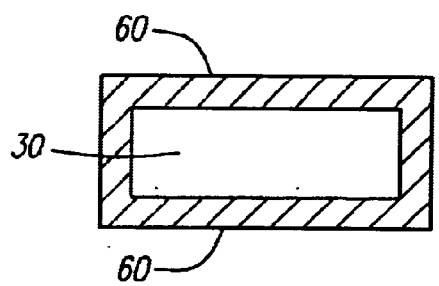
FIG. 4
FIG. 5
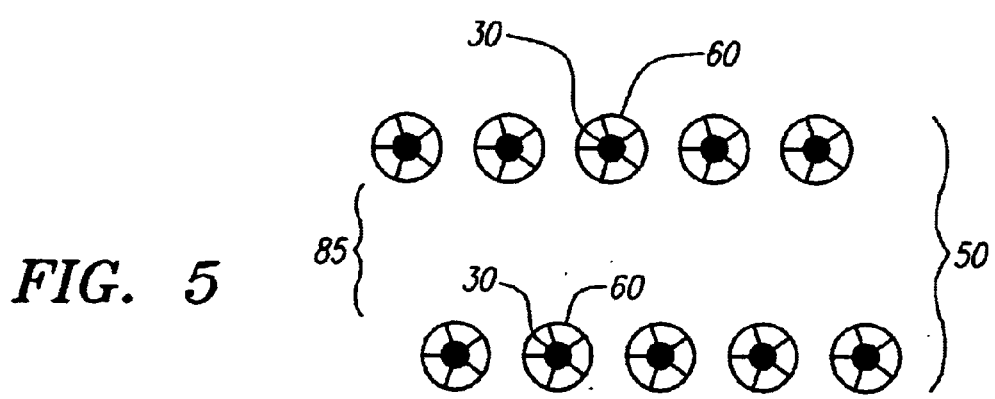

METHOD AND APPARATUS CREATING A RADIOACTIVE LAYER ON A RECEIVING SUBSTRATE FOR IN VIVO IMPLANTATION

CROSS REFERENCE TO RELATED APPLICATIONS

This application is a divisional application of commonly assigned application Ser. No. 08/987,794 invented by Michelangelo Delfin and Mary E. Day and filed Dec. 10, 1997, now U.S. Pat. No. 6,129,658 which is incorporated herein by reference.

FIELD OF THE INVENTION

The present invention relates to implantable medical apparatus, especially radioactive stents for reducing the incidence of restenosis, and to a method for imparting radioactive properties to substrate materials such as stents, in particular by creating a surface layer of a radioactive isotope such as $^{32}$P.

BACKGROUND OF THE INVENTION

A variety of apparatus and techniques have been developed for treating stenotic sites within body lumens. Among these apparatus and techniques are balloon dilitation and plaque excision. Among known balloon dilitation devices are coronary, peripheral vessel, bile duct and thorasic catheters. In balloon dilitation, a catheter equipped with an expandable balloon is threaded intravascularly to the site of atherosclerotic narrowing of the vessel. Balloon dilitation is known to have a good success rate in enlarging constricted body lumens, although there are various theories explaining the precise effect on constrictions causing this enlargement. Known plaque excision devices include ultrasound and mechanical excision devices. Plaque excision devices typically operate to remove or reduce in size at least a portion of the plaque associated with a stenotic region.

One complication of the known treatments of stenotic regions is restenosis (i.e. re-narrowing) of the vessel following treatment. Among the causes of such restenosis are, intimal hyperplasia (excessive tissue growth) and thrombus accumulation. It is known to reduce the occurrence of restenosis by placing a stent device at the site of the treated region. However, even with a stent in place, restenosis is known to occur in some treated sites, such as by the occurrence of excessive tissue growth.

The use of radiation to treat such excessive tissue growth also is known. A variety of techniques for delivering radiation to stenotic sites have been developed. One such technique delivers a radioactive dose via catheter, prior to stent implantation. An example of such a technique is described in Waksman et al., "Intracoronary Radiation Before Stent Implantation Inhibits Neointimal Formation In Stented Porcine Coronary Arteries," *Circulation*, 1995:92:1383–1386. In this example, a low-dose radiation is delivered to coronary arteries from a radioisotope source, such as $^{192}$Ir or $^{90}$Sr/Y, via a catheter.

Another way of applying radiation to inhibit restenosis is through the use of radioactive stents. Examples of radioactive stents are described, in U.S. Pat. No. 5,059,166 and U.S. Pat. No. 5,213,561. Such known radioactive stents are made by various processes, such as by having a spring coil stent material irradiated so that it has become radioactive, implanting into a stent spring wire a radioactive ion such as phosphorous 32, alloying a stent spring wire with a radioactive ion, forming a stent coil from a radioisotope core material which is formed within an outer covering, and plating a radioisotope coating (such as gold 198) onto a stent spring material core.

A disadvantage of the known radioactive stents is undue complexity in the manufacturing process making the manufacture and handling of such stents difficult. Some known techniques of irradiating stent materials suffer the disadvantage of requiring the use of the neutron beam of a nuclear reactor in conjunction with an ion-implanter equipped with a sublimation source. One such example is described in Hehrlein, et al., "Pure β-Particle-Emitting Stents Inhibit Neointima Formation in Rabbits," *Circulation*, 1996:93:641–645. Other known techniques involve high temperatures above the melting points of the materials being used to manufacture the stents, such as alloying.

Because of the complexity of the manufacturing processes, known manufacturing techniques suffer further disadvantages of being relatively unsuited for distributed manufacturing, in that the equipment costs are relatively high and the necessary manufacturing equipment such as wire forming equipment, alloying equipment, reactors and/or plating equipment is not understood to be readily transportable and requires operation by operators having skill in operating the equipment.

Yet another disadvantage of the known manufacturing techniques is the transport time between the site of manufacture and the site of use. Because of the need for transport of stents, at least some of the radioactive dose imparted during the manufacturing process is lost, since it is desirable to use if radioactive materials having relatively short half lives. With a radioisotope having a half-life of approximately fourteen days, such as $^{32}$P, approximately 78% of the radioactive dose remains after five days and 62% of the radioactive dose remains after ten days. Materials having shorter half lives are desired so that the radioactive effect of an implanted device dissipates relatively quickly, leading to greater control of the term of radioactive exposure of the patient. In order to compensate for the undesirable transport times and distances using the known techniques, users may need to resort to the use of radioactive materials having longer half lives, or to imparting greater radioactive doses to the stent material during manufacture, in order to compensate for the delays between manufacture and use such as in hospitals. This leads to increased inefficiency and cost.

Metal-phosphate coating processes using phosphoric acid solutions are also known for depositing coatings of to prevent corrosion, lubricate, prolong the life of metal surfaces, and improve paint coating adhesion. However, they have not been found well-suited to the specialized needs of medical applications such as stents or stent materials. Briefly described, the metal surface chemically reacts with a phosphate solution, forming a phosphate layer on the metal's surface, which is either amorphous or crystalline depending on the operating conditions. A disadvantage of this coating technique is that the phosphate coating does not have the structural integrity required in medical uses and the has undesirable degrading or flaking characteristics. In addition, the transition metal (abbreviated herein as "m") phosphate coating is generally a primary (i.e., $mH_2PO_4$), secondary (i.e., $m_2HPO_4$), or tertiary (i.e., $m_3PO_4$) metal phosphate, all of which are often hydrated (i.e., $m_{3-n}H_nPO_4 \cdot xH_2O$, where x=1, 2, 3, . . .).

From the above, it is apparent that there is a need for a more economical technique to manufacture radioactive stents, using less complex manufacturing processes and for an improved construction of a radioactive stent and for an improved method of manufacturing radioactive stents. It is therefore an object of the present invention to provide a method of making radioactive stents which can be performed at distributed sites, such as within or close to hospitals or other facilities where they may be used.

It is another object of the present invention to provide a method of making radioactive stents in a manner that could be done within the hospital or facility on an as-needed basis.

It is a further object of the present invention to provide a more economical method of making radioactive stents requiring less complicated techniques and apparatus.

Another object of the present invention is to provide a method of making a radioactive stent and for manufacturing a radioactive stent having increased accuracy in determination of the radioactive dose control, and achieving a greater degree of dosage uniformity that is independent of the stent geometry in the manufacturing process.

A further object of the present invention is to provide a stent coated with a radioisotope, which coating layer is generally insoluble as used for in vivo implantation.

Yet another object of the present invention is to provide a radioactive stent that includes a radioactive isotope material chemically bonded with a base material.

SUMMARY OF THE INVENTION

The present invention alleviates to a great extent the disadvantages of the known systems for manufacturing radioactive materials, such as stents for in vivo implantation by providing a method and apparatus for forming a layer containing a radioactive isotope received on a substrate or base material. A solution preferably including a polymerized chain including the radioactive isotope is provided. The solution is contacted with the substrate material and the substrate material receives the radioactive isotope containing layer.

In a preferred embodiment, the solution includes a polymerized orthophosphoric acid solution enriched with phosphorous-32 ($^{32}P$). The substrate, preferably is a preformed medical stent, or alternatively a base material suitable for formation into a useful device, such as a stent. In operation, the substrate is immersed in the solution for a desired amount of time so as to impart a radioactive layer including phosphorous-32 to the substrate. The radioactive dosage is controlled by controlling the reaction time and other reaction conditions such as temperature and solution concentration.

Any stent shape or construction may be used in conjunction with the present invention.

The radioactive layer is formed on the surfaces in proximity to the solution, i.e. the surfaces which were contacted by solution. In embodiments where the stent is immersed in the solution, the radioactive layer is received on all the exposed surfaces. For example, where the stent has an open tubular structure, the radioactive layer is deposited on the inside and outside surfaces. In the preferred embodiment, where phosphorous-32 is used as the radioactive isotope, preferably a phosphorous-oxygen-phosphorous network bonding the phosphorous-32 to the substrate is formed.

The above and other objects and advantages of the invention will be apparent upon consideration of the following detailed description, taken in conjunction with the accompanying drawings in which like reference characters refer to like parts throughout.

BRIEF DESCRIPTION OF THE DRAWINGS

FIG. 3A is a cross section of a tubular stent in accordance with the present invention;

FIG. 3B is a partial cross section of a tubular stent in accordance with the present invention, taken along line B—B of FIG. 3A;

FIG. 4 is a cross section of a filament-type base material in accordance with the present invention;

FIG. 5 is a cross-section of a coil stent in accordance with the present invention;

DETAILED DESCRIPTION OF THE INVENTION

In accordance with the present invention, a radioactive material or a radioactive medical device such as a stent for in vivo implantation is created by creating a radioactive layer on a substrate by treating a base material 30 with a solution 20 containing a radioactive isotope transferring substance. The radioactive isotope is received by the base material 30 forming a layer in which the radioactive isotope is received in the base material 30. In this description, the terms "base material" or "substrate" or "substrate material" will each be used to refer to the material receiving the radioactive isotope. Any substance that will receive the radioactive isotope may be used as such a base material, substrate or substrate material. It is preferred that this substance be capable of receiving the coated radioactive substance in a relatively non-degradable manner so as to minimize degradation or flaking in use.

Figure 1:
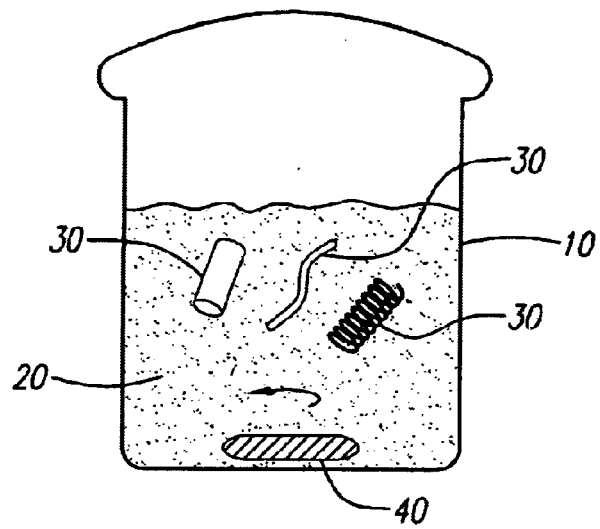
FIG. 1 is a diagram of an exemplary apparatus in accordance with the present invention.

In addition, the substrate material may be formed into any shape. It may be in a form adapted for later formation into a useful object such as a stent, or it may be pre-formed into such a useful object. For example, the substrate material may be in the form of a filament, wire, mesh, lattice, coil, foil, plate, or other shape. It is preferred that the substrate material 30 be formed into a stent, either prior to or subsequent to contact with the solution 20 and accordingly it is preferred that the substance selected as the substrate material be suitable for in vivo implantation in a body lumen. In this context it is also desirable that the radioactive isotope received in the base material 30 be adhered in a fashion that will withstand degradation, such as by dissolution or flaking upon placement in a body lumen. The substrate material 30 also is preferably formed into a stent or other useful structure prior to treatment with the solution 20. FIG. 1 depicts illustrative examples of substrate material 30 shapes including, from left to right a generally tubular stent, a filament and a coil.

Any substance may be used for the substrate material 30 as long as it can receive the radioactive material in solution 20. In a preferred embodiment, the substrate material 30 is made of a metallic material capable of receiving the deposit of $^{32}$P containing phosphate from solution 20. Any suitable metallic material or combination of metallic materials may be used, such as by way of example tungsten, aluminum, metal alloys, stainless steel, (including any of numerous iron based alloys) tantalum, rhenium, titanium, or other types of metallic materials. Alternatively, non-metallic materials, composites of metallic and non-metallic materials or other composites may be used. By way of illustration, metal-plastic, metal-ceramic composites may be used, and non-metals such as rubbers, ceramics, plastics or other polymers may be used as long as the radioactive material can be received by at least a portion of the substrate.

Figure 2A:
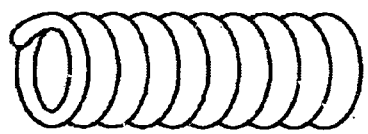
FIG. 2A is an illustration of a coil stent in accordance with the present invention.
Figure 2B:
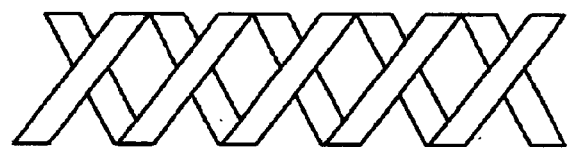
FIG. 2B is an illustration of a mesh stent in accordance with the present invention.
Figure 2C:
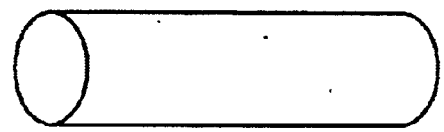
FIG. 2C is an illustration of a tubular stent in accordance with the present invention.

Any form of stent may be fabricated using the process of the present invention, so long as the stent can perform the function of placement within a body lumen and retaining a required profile for a sufficient period as required for the desired treatment. Examples of suitable stent structures include a coil stent 52, illustrated in FIG. 2A, a mesh or lattice stent 54, as illustrated in FIG. 2B and a tubular stent structure 56, illustrated in FIG. 2C.

Likewise, any structure of the substrate material, 30 prior to treatment with the radioactive isotope transferring solution 20 may be used, so long as it is compatible with the apparatus used for treating the substrate material 30 with the solution 20. In the illustrated preferred embodiment, the solution 20 is within a container 10 and the substrate material is placed within the solution 20 bath in the container 10. Any form of container 10 may be used that can contain the solution 20 and receive the substrate material 30. As the solution 20 contains a radioactive material, it is preferred that the container 10 be adapted to the special handling requirements for storing or processing radioactive substances. Depending upon the radioactivity source, it may be desirable to for some portion, such as the outside of the container 10 to be made of a radioactivity blocking material, such as lead. Alternatively, or in addition, the container 10 may be housed within a blocking enclosure (not shown). Any apparatus may be used for placing the substrate material 30 within the container 10. For example, tongs, grippers, automated movers or manual insertion may be used.

Exemplary stent materials fabricated in accordance with the present invention are illustrated in FIGS. 3A, 3B, and 5. A stent 50 having a generally circular cross section is illustrated in FIGS. 3A and 3B. The substrate 30 has a generally circular profile, defining a generally circular hole within the circular substrate 30 structure. Such a substrate may be formed in the shape of an open or capped tube. In the illustrated embodiment, the substrate is an open tube. As illustrated in the section taken along line B—B, shown in FIG. 3B, radioactive layers 60 are formed on the outside portion 70 and inside portion 80 of the substrate 30. In a sealed closed tube substrate 30, the solution 20 containing a radioactive material depositing substance will not contact the inside portion 80 and accordingly radioactive layer 60 is not formed. In the illustrated embodiment, solution 20 contacts the inside portion 80 and a radioactive layer 60 is formed. A tubular aperture 85 is also defined. In use as a stent, this aperture allows the flowthrough of a body fluid, such as blood or air.

A second example is illustrated in FIG. 4. In this example, the substrate 30 is a solid filament having a rectangular cross-section. The radioactive layer 60 is situated on the outside of the substrate 30. Any shape filament may be used which can receive the radioactive material. For example, filaments having round, oval, square, diamond, hexagon, etc. cross-sections may be used. In addition, hollow filaments may be used, again having any desired cross-section. In a preferred embodiment, the substrate filament is made of a metallic material capable of receiving the deposit of $^{32}$P containing phosphate from solution 20, although any material receiving the desired radioactive material may be used. Various forms of stents may be formed of filament materials. One example is the mesh stent illustrated in FIG. 2B. Preferably such a filament based product is formed prior to contact with the solution 20. In the case of the mesh stent, a radioactive layer 60 is formed about the filaments forming the stent in the fashion illustrated in FIG. 4. It should be understood that in some stent constructions, individual filaments are in close proximity or bonded with one another, and at such points where solution 20 does not come into contact with the filaments, a radioactive layer is not formed.

An example of a coil stent 50, shown in cross-section is illustrated in FIG. 5. In this example, the substrate material 30 is a coiled filament having a solid cross section. The radioactive layer 60 is situated on the outside of the substrate material 30. In cross section, a plurality of coils are shown having discrete generally round cross sections. The coils define a substantially tubular aperture 85 through which a bodily fluid may flow.

In the preferred embodiment, a metallic stent is used as a substrate 30 and is immersed in solution 20. The metallic stent has a layer containing phosphorous-32, causing it to become both radioactive and chemically inert when placed within a body lumen. Preferably a beta radiation emitter having a relatively short half-life is used—as is generally preferable in short term medical implantations. Radioactive materials having half lives of approximately 100 days or shorter are preferred, although any longer half lives may be selected depending on the desired application. One such alternative material is strontium-89. The $^{32}$P isotope is generally understood to be such a β-emitter, having a half-life of approximately 14.3 days and an average beta emission of 0.694 MeV. Examples of substrate materials suitable for stent applications include stainless-steel (including any of numerous iron based alloys), tantalum, rhenium, titanium and an alloy such as nitinol (for example, 55% by weight nickel and 45% by weight titanium), composite materials containing metals and non-metals or multiple metallic or non-metallic materials, alloys having multiple metallic or non-metallic materials, plated materials having plural layers of different materials, ceramics, plastics or other polymers, rubber or any other material suitable for percutaneous insertion.

As noted above, other embodiments of the present invention use other suitable radioactive isotopes. One example is strontium-89 with a half-life of approximately 50.5 days and beta emission of 1.463 MeV. In this embodiment, the radioactive strontium-89 can be supplied in an aqueous SrCl$_2$ (strontium chloride) solution. In the illustrated embodiment, therefore, the solution 20 may include such an aqueous SrCl$_2$ solution and/or a radioactive strontium enriched SrCl$_2$ solution, although any suitable strontium depositing solution may be used.

Figure 6A:
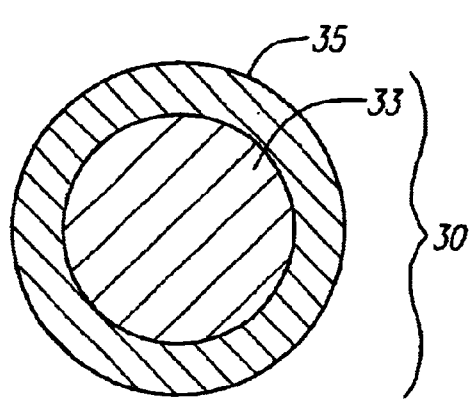
FIG. 6A is a cross section of an embodiment of a multi-layer substrate in accordance with the present invention.
Figure 6B:
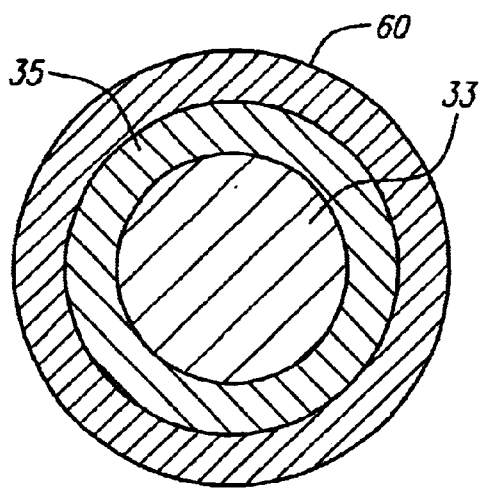
FIG. 6B is a cross section of an embodiment of a multi-layer substrate having a radioactive layer in accordance with the present invention.

Alternatively, other materials having a relatively low affinity for the radioactive isotope, i.e. $^{32}$P in the preferred embodiment, may be used. If such a material is used, the device, or substrate material made of such a low affinity material may be pre-treated or coated with another material having a greater affinity for the radioactive isotope, such as stainless steel or nitinol. As illustrated in FIGS. 6A and 6B, the substrate material 30 includes a first material, forming a first substrate layer 33, and a second material coated upon it, forming a second substrate layer 35. Radioactive layer 60 is formed on the second layer 35. In this embodiment, the first layer 33 of the substrate material 30 is made of the first material may have a relatively low affinity for the radioactive isotope while the second layer 35 may have a higher affinity for the radioactive isotope. Alternatively, the materials may have similar affinities for the radioactive isotopes, but use of different substrate layer materials may be desired to achieve favorable handling properties. The multi-layer substrate in accordance with this embodiment may be formed using any technique, such as core-forming and plating. In one example, the first material forming the first layer 33 is a non-metallic material, such as rubber, ceramic, plastic or other polymer and the second material forming the second layer is a metallic material.

In accordance with a preferred embodiment of the present invention, the radioactive material forming the layer 60 received by the substrate material 30 includes condensed, or polymeric, phosphates. Such condensed or polymeric phosphates are suitable for in vivo use as such relatively high molecular weight phosphates (as compared with primary, secondary or tertiary phosphates) are less water soluble, less soluble in dilute acidic or alkaline solutions, and more chemically inert.

The method of the invention will now be described in greater detail. A solution 20 containing a radioactive isotope adapted to be received as a radioactive layer 60 on a substrate 30 is formed. The solution 20 is contacted with the substrate material by any suitable technique, such as immersion, spraying, brushing or dipping for a period of time. The length of contact of the substrate 30 with the solution 20 is determined by the amount of radioactive dosage desired, although other factors also influence the radioactive dosage. Longer contacts generally will result in a higher dosage. Likewise shorter contacts will generally result in a lower dosage. The radioactive dosage also can be influenced by factors such as solution concentration, radioactive material selected, amount of surface area receiving the radioactive material and so on.

Following contact with the solution 20, the now treated substrate 30 may be subjected to additional finishing treatment, such as to harden, soften or otherwise improve the properties of the treated material. For example, cooling, quenching and/or rinsing with deionized water may be performed.

In the preferred embodiment, the solution 20 is placed in an apparatus including container 10 adapted to receive and contain the solution 20. The apparatus also may optionally include an agitating device 40 for agitating, stirring or otherwise moving the solution 20 while in the container 10. It is preferred that the solution 20 be agitated in some fashion so as to increase the fluid flow about, around and/or within the substrate material 30 placed within the solution. In the embodiment illustrated in FIG. 1, a rotating agitator 40 is shown. The agitator 40 spins so as to stir the solution 20. Alternatively, the apparatus and/or the container 10 may be moved so as to agitate the solution contained in it. For example, the container 10 may be vibrated using a vibrating mechanism. Alternatively, the container may be spun, wobbled or translated linearly back and forth or in any other pattern of motion.

In the preferred embodiment, the solution 20 contains a radioactive phosphorous isotope, preferably phosphorous-32. The solution preferably includes a phosphorous-32 containing polyphosphoric acid bath of the general formula:

$$H_{(n+1)}P_nO_{(3n+1)} \qquad (1)$$

where n>2 meaning there are at least three or more phosphorous atoms in the molecular structure, however, any derivative of polyphosphoric acid will suffice. Preferably a concentrated solution is created in which the density is greater than 1.95 g/cm$^3$. The polyphosphoric acid solution typically contains $P_2O_5$ as a reactant. Any concentration of the $P_2O_5$ reactant within the solution may be used which will result in the release of the desired amount of phosphate ions for reaction with the substrate material. An example of a preferred concentration is greater than 79% on a weight basis and less than 85% on a weight basis although any other suitable concentration may be used as well. It is understood for example that polyphosphoric acids with $P_2O_5$ concentrations between approximately 85% and 90% on a weight basis are suitable for use in conjunction with our invention but because such higher concentration solutions generally have an increased viscosity handling can be more difficult. The treatment solution preferably is heated to greater than 260° C. and less than 350° C., although it should be understood that any temperature suitable for facilitating the chemical reaction may be used. The result achieved using this solution is the deposit upon the substrate of a chemically inert, hardened transition metal-phosphate layer.

The radioactive dosage imparted to a patient is regulated by controlling the amount of the radioactive isotope deposited. For example, a relatively thick layer 60 of radioactive isotope will result in a greater dosage compared with a relatively thin layer when the layers have the same radioactive density. The dosage also can be controlled with great precision in this way. A generally thicker radioactive isotope layer 60 can be deposited by using a greater immersion time or using increased agitation, as compared with a thinner layer 60, which would use a shorter immersion time and/or decreased agitation of the solution 20.

Figure 7:
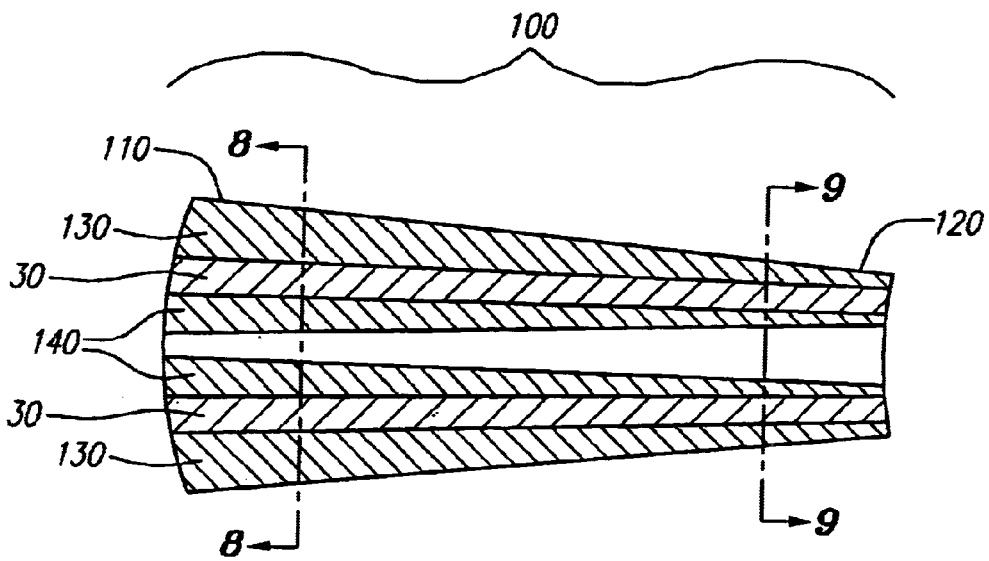
FIG. 7 is an axial cross section of a non-uniform dosage stent in accordance with the present invention.
Figure 8:
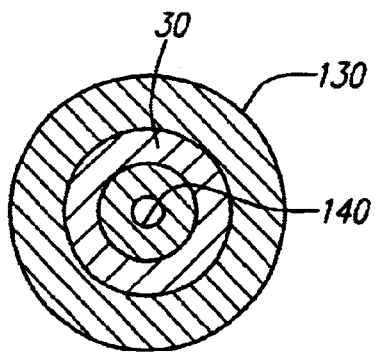
FIG. 8 is a cross-section of the non-uniform dosage stent taken from line A—A of FIG. 7.
Figure 9:
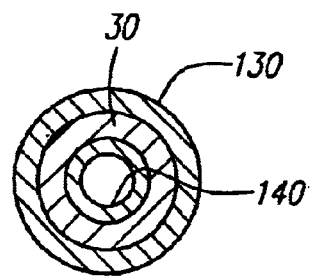
FIG. 9 is a cross-section of the non-uniform dosage stent taken from line B—B of FIG. 7.

In addition, uniform or non-uniform radioactive layers 60 can be created. For example, the radioactive layer 60 can be thicker on one portion of the substrate 30 than on other portions of the substrate 30. These uneven radioactive layers are formed by unevenly applying the solution 20 to the substrate 30. For example, in the preferred stent embodiment, a uniform layer 60 may be created by fully immersing the substrate material 30 (in the form of a stent) in the solution 20. Alternatively, a non-uniform radioactive layer 60 can be formed by unevenly applying the solution, such as by dipping one portion of the substrate 30 in the solution 20 for a different time period than another portion. As illustrated in FIG. 7, in accordance with this embodiment, a generally tubular stent 100 has a first end 110 and second end 120. The first end 110 is contacted with solution 20 for a longer period of time than the back end 120, resulting in a non-uniform outer radioactive layer 130 and inner radioactive layer 140. FIGS. 8 and 9 illustrate cross-sections, taken along lines A—A and B—B of FIG. 7, respectively. In one embodiment, the first end 110 is dipped in solution 20 for a longer period of time than the second end 120, resulting in generally thicker radioactive layers 130, 140 at the first end 110 than at the second end 120. Any desired layer profiles may be created as well. For example, a radioactive layer 60, may be deposited only at one end, or at the two ends, but not in the middle.

Likewise, non-uniform radioactive dosages may be imparted to a substrate 30 using solutions depositing layers having different radioactive densities. For example, a dense layer may be created at one location on a substrate 30 by dipping in a solution 20 that deposits a layer having a higher radioactive dosage than a second solution provided for another location on the substrate 30. In this embodiment any number of solutions and applications may be used. For example, when two solutions are desired, a first solution having a first radioactive concentration is provided and a second solution having a different radioactive concentration is provided. Different concentrations of a particular radioactive isotope can attain these different concentrations. Alternatively, use of different radioactive isotopes in the different solutions may attain these different concentrations.

Other embodiments of non-uniform dosages involve, for example, first immersing the substrate 30 in a solution 20 and then dipping only a portion of the substrate in the solution 20, creating a different dosage profile in the dipped portion than in the remainder of the substrate 30.

The solution 20 is preferably formed by providing a solution base containing a solution of a substance capable of bonding with phosphorous-32 (i.e. $^{32}P$) in polymerization reactions. Preferably this is a solution of orthophosphoric acid, $H_3PO_4$. Then the solution base is dehydrated until a desired degree of polymerization is achieved. It should be noted that any technique of polymerization can be used such that compounds of high molecular weight, e.g. polymers, are created from the smaller molecules (monomers) in the original solution. Such reactions can include the addition of one molecule to another (addition reactions) or the elimination of a small molecule such as water or alcohol (condensation reactions). Preferably, the orthophosphoric acid is enriched with $^{32}P$ prior to the polymerization process, causing the solution to become radioactive.

In one example, orthophosphoric acid $H_3PO_4$ supplied as an 85 weight % aqueous solution having a nominal density of 1.7 g/cm$^3$. An excess 15% water was removed via thermal dehydration. In one example, dehydration was performed at 120° C., although any temperature may be used which will result in reduction of water content from the solution. As the water content is decreased the pure acid that remains initiates a polymerization reaction as follows:

$$nH_3PO_4 => H(HPO_3)_nOH + (n-1)H_2O \qquad (2)$$

in which $H_2O$ continues to be evaporated causing the acid to be further polymerized, as the dehydration process continues. The degree of polymerization is proportional to the proportion of $P_4O_{10}$ in solution. Linear polyphosphoric acids in accordance with formula (1) above are produced first with n=2. As dehydration continues, the value of n increases such as to 3, 4, 5 or higher, indicating a greater degree of polymerization as the value of n increases. The rate of dehydration increases as temperature increases. Dehydration may be performed at any temperature where the amount of water in solution can be reduced, such as, for example between 120° C. and 500° C. Preferably dehydration is performed at approximately 300° C. for greater ease of handling. Adding a $^{32}P$ enriched source prior to dehydration allows isotope exchange to occur in the course of the hydrolytic disproportion reaction illustrated in equation (2) above.

Any phosphorous-32 source may be used. One commercial source is $^{32}P$ enriched sodium orthophosphate in a water solution containing approximately 1 mg formaldehyde/ml. from Amersham Corporation, 2636 S. Clearbrook Drive, Arlington Heights, Ill. Another commercial source is $^{32}P$ enriched sodium pyrophosphate with $SnCl_2$ from Mallinkrodt Laboratory Chemicals, 222 Red School Lane, Phillipsburg, N.J. In operation of the present invention, the $^{32}P$ source may be directly mixed with the polyphosphoric acid.

Alternatively $^{32}P$ enriched orthophosphoric acid can be used. One example is an orthophosphoric acid in a 0.01N HCl solution with a radionuclide purity of greater than 99.5% from MDS Nordion, 447 March Road, Kanata, Ontario Canada K2K 1X8 (613-592-2790). In mixing with the polyphosphoric acid, some of the chlorine (Cl) will normally substitute for an hydroxide (OH) forming a phosphorous-chlorine (P—Cl) bond.

The polymerized polyphosphoric solution thus formed can be stored as well, with the desired concentrations maintained, such as by refluxing vapor or any other suitable method as well. Because of the relatively short half life of the radioactive isotope used in this example, additional radioactivity source material may need to be added prior to use, if the solution is stored for a long period of time.

In the preferred embodiment, during the reaction process, the solution 20 chemically reacts with the substrate 30 preferably forming a relatively thin, chemically inert, hardened transition surface layer with a chemical composition consisting of oxygen, metal and phosphorous. The thickness and chemical ratios of the phosphate-coating will differ depending upon the particular material used for the substrate 30. In general, it has been found that a phosphorous-oxygen-phosphorous ("P—O—P") network is formed in the reacted layer in which the P—O—P network is bonded to substrate molecules. For example, linear pholyphosphates having the general formula $$[P_nO_{(3n+1)}]^{(n+2)-} \qquad (3)$$

and cyclic polyphosphates having the general formula $$[P_nO_{3n}]^{n-} \qquad (4)$$

can form, with the particular polyphosphate formed depending on the proportion of $P_4O_{10}$ in solution. The stoichiometry of the condensed phosphate generally depends upon the oxidation state of the substrate 30. For example, where a metal substrate, such as titanium, is used, the oxidation state of the metal will be the highest oxidation state. In the titanium example, $Ti^{4+}$ is greater than $Ti^{3+}$, which is greater than $Ti^{2+}$, and so on. In addition, in general, the amount of phospatization will generally increase as temperature increases.

In the embodiment using a solution depositing strontium-89, it is preferred that the strontium-89 is incorporated as a Sr—O bond in the reacted layer. The strontium chloride solution is added until a desired amount of polymerization is achieved.

Any radioactive isotope can be used to combine with the treatment solution. However, pure-emitters have a distinct advantage over the use of energetic-emitters in that -particles have a limited penetration in tissue and deliver significantly less dose beyond the prescription point than do-emitters. A radioactive isotope with relatively short half-life, such as the radioactive isotope $^{32}P$, is preferred for stent applications because radiation is no longer necessary or desirable after the unwanted tissue stops its growth. Having a short half-life also advantageously limits the whole-body exposure to the patient and to the operator.

In one embodiment practicing the present invention, substrates 30 made of foils of titanium or rhenium are immersed within a polymerized orthophosphoric acid solution 20 within a container 10 for approximately 30 to 60 seconds at ambient temperature (approximately 22° C.). The substrates receive a coating including oxygen, the base metal and the radioactive isotope phosphorous. A phosphorous-oxygen-phosphorous (P—O—P) network is bonded to the metal having a characteristic x-ray photoemission spectrum with a phosphorous ($2p_{3/2}$) binding energy of approximately 133.9 eV using the carbon (1s) transition centered at approximately 284.6 eV as a reference. Other binding energies may be found, depending largely on the extent of networking and the composition of the substrate material and the radioactive isotope used. In this embodiment, the (3/2 to 1/2) splitting energy is 1.0 eV. In a preferred embodiment, neither concentrated HCl nor concentrated $HNO_3$ will etch tantalum and nickel surfaces that have been phosphatized as described in this description at room temperature.

Thus, it is seen that a method for efficiently producing radioactive isotope coated substrates suitable for medical application is provided. One skilled in the art will appreciate that the present invention can be practiced by other than the preferred embodiments, which are presented in this description for purposes of illustration and not of limitation, and the present invention is limited only by the claims that follow. It is noted that equivalents for the particular embodiments discussed in this description may practice the invention as well.

What is claimed is:

1. A method of making a radioactive stent comprising:
   forming a non-radioactive stent;
   providing a solution containing a polymerized phosphorous-32 depositing material in solution; and
   placing at least a portion of the stent in contact with at least a portion of the solution forming a P—O—P network at the surface of the stent in proximity to the portion of the stent placed in contact with the solution which P—O—P network bonding phosphorous-32 to the stent.

2. The method as described in claim 1 wherein a first section of the stent has a greater amount of phosphorous-32 than a second section of the stent.

3. The method as described in claim 2 wherein the second section has at least some phosphorous-32, and wherein the first section is made to have a greater amount of the phosphorous-32 by one or more of: using different reaction times for the first section and the second section, using different reaction conditions for the first section and the second section, or using different concentrations of the phosphorous-32 in the solution for the first section and the second section.

4. A radioactive stent for use in treating stenotic sites, formed using a method comprising:
   providing a solution containing a radioactive isotope containing substance within the solution;
   providing a substrate material, the substrate material being capable of chemically bonding with the radioactive isotope containing substance from the solution;
   treating at least a portion of the substrate material with the solution wherein the radioactive isotope containing substance bonds directly to the substrate material and the radioactive isotope on the portions of the substrate material that are treated with the solution has a dosage for effecting radioactive treatment of the tissue; and,
   forming the substrate material into a stent.

5. A radioactive stent for use in treating stenotic sites, formed using a method comprising:
   providing a solution containing a radioactive isotope containing substance within the solution,
   providing a substrate material, the substrate material being capable of receiving the radioactive isotope containing substance from the solution; and
   treating at least a portion of the substrate material with the solution forming a layer of material bonded to the substrate material and containing the radioactive isotope on the portions of the substrate material that are treated with the solution, wherein the stent has a longitudinal dimension, and wherein a first longitudinal section of the stent has a greater amount of the radioactive isotope than a second longitudinal section of the stent.

6. A radioactive stent for use in treating stenotic sites formed using a method comprising:
   providing a solution containing a radioactive isotope deposit substance within the solution;
   providing a substrate material the substrate material being cable of receiving a radioactive isotope containing substance from the solution and
   treating at least a portion of the substrate material with the solution forming a layer of material bonded to the substrate material and containing the radioactive isotope on the portions of the substrate material that are treated with the solution, wherein a first section of the stent has a greater amount of the radioactive isotope than a second section of the stent, and wherein the second section has at least some radioactive isotope, and wherein said first section is made to have a greater amount of the radioactive isotope by one or more of: using different reaction times for the first section and the second section, using different reaction conditions for the first section and the second section, or using different concentrations of the radioactive isotope in the solution for the first section and the second section.

\* \* \* \* \*